(12) United States Patent
Polonsky et al.

(10) Patent No.: US 8,438,903 B2
(45) Date of Patent: May 14, 2013

(54) MOLECULE DETECTION DEVICE FORMED IN A SEMICONDUCTOR STRUCTURE

(75) Inventors: Stanislav Polonsky, Putnam Valley, NY (US); Frank Suits, Garrison, NY (US)

(73) Assignee: International Business Machines Corporation, Armonk, NY (US)

( * ) Notice: Subject to any disclaimer, the term of this patent is extended or adjusted under 35 U.S.C. 154(b) by 265 days.

(21) Appl. No.: 12/694,712

(22) Filed: Jan. 27, 2010

(65) Prior Publication Data

US 2011/0179852 A1 Jul. 28, 2011

(51) Int. Cl.
*G01N 30/02* (2006.01)
*G01N 30/26* (2006.01)
*C12M 1/34* (2006.01)

(52) U.S. Cl.
USPC .................................. 73/23.4; 435/288.5

(58) Field of Classification Search .................. 73/23.36, 73/23.39, 23.4, 23.41; 435/288.5
See application file for complete search history.

(56) References Cited

U.S. PATENT DOCUMENTS

| | | | |
|---|---|---|---|
| 4,908,112 | A | 3/1990 | Pace |
| 6,685,841 | B2 | 2/2004 | Lopez et al. |
| 7,351,648 | B2 | 4/2008 | Furukawa et al. |
| 7,465,381 | B2 | 12/2008 | Lopez et al. |
| 2003/0098419 | A1 | 5/2003 | Ji et al. |
| 2003/0226604 | A1 | 12/2003 | Schlautmann et al. |
| 2007/0141599 | A1 | 6/2007 | Quake et al. |
| 2007/0238112 | A1* | 10/2007 | Sohn et al. ........................ 435/6 |
| 2009/0178935 | A1* | 7/2009 | Reymond et al. .......... 205/777.5 |

FOREIGN PATENT DOCUMENTS

WO WO2008/127438 A2 10/2008
WO PCT/US2010/057146 1/2011

OTHER PUBLICATIONS

M.H.R. Lankhorst et al., "Low-Cost and Nanoscale Non-Volatile Memory Concept for Future Silicon Chips," Nature Materials, Apr. 2005, pp. 347-352, vol. 4, No. 4.
M. Schlund et al., "Continuous Sampling and Analysis by On-Chip Liquid/Solid Chromatography," Sensors and Actuators B: Chemical, Oct. 2006, pp. 1133-1141.
J.W.F. Robertson et al., "Single-Molecule Mass Spectrometry in Solution Using a Solitary Nanopore," Procedures of the National Academy of Sciences of the United States of America, May 2007, pp. 8207-8211, vol. 104, No. 20.
S. Van Dorp et al., "Origin of the Electrophoretic Force on DNA in Solid-State Nanopores," Nature Physics, Mar. 2009, pp. 347-351, vol. 5, No. 5.

* cited by examiner

*Primary Examiner* — Lisa Caputo
*Assistant Examiner* — Punam Roy
(74) *Attorney, Agent, or Firm* — Vazken Alexanian; Ryan, Mason & Lewis, LLP

(57) ABSTRACT

Semiconductor devices, chromatography devices and integrated circuits for detecting one or more molecules and methods for forming a semiconductor device for detecting one or more molecules are presented. For example, a semiconductor device for detecting one or more molecules includes a channel formed within a semiconductor structure, and at least one detector formed within the semiconductor structure. The at least one detector detects the one or more molecules in the channel. The semiconductor device may optionally comprise one or more additional channels formed within the semiconductor structure. The semiconductor device may, for example, be operative to detect a single molecule.

23 Claims, 4 Drawing Sheets

100

100

200

200

500

600

700

800

900

MOLECULE DETECTION DEVICE FORMED IN A SEMICONDUCTOR STRUCTURE

FIELD OF THE INVENTION

The present invention relates generally to small-scale systems for detecting, quantifying, identifying and/or separating molecules and, more particularly, to planar nano-channels and detectors formed in a semiconductor structure.

BACKGROUND OF THE INVENTION

Chromatography is a technique for separating mixtures. A mixture may comprise two or more components, for example, two or more different molecules or chemical compounds. The mixture may further comprise a solvent for solubilizing the two or more components (solutes). In chromatography, the dissolved mixture is known as a mobile phase. Note that the term "phase," as used herein in the terms mobile phase and stationary phase, means a physically distinctive form of a substance. A mobile phase signifies movement or mobility of the substance (i.e., the dissolved mixture). A stationary phase signifies that the substance of the stationary phase is not mobile. Chromatography involves passing the mobile phase through a stationary phase. The stationary phase is part of the device performing the chromatography (chromatography device) and separates the analyte to be measured from the other components in the mixture, based on differential partitioning between the mobile phase and the stationary phase. Components in a sample mixture injected into the chromatography stationary phase travel different distances based on how strongly they interact with the stationary phase. Retention time of a single molecule or other component inside a chromatography channel is indicative of the properties of the molecule or other component such as hydrophobicity or size. Further, the specific retardation time of a particular component passing through a chromatography channel can be used to identify the component.

Chromatographic technologies are essential to life sciences research, as they are useful in both the purification of pharmaceutical products and in analytical assays. Detectors coupled to the chromatography device are able to produce a signal that is plotted against retention time to produce elution peaks. Analysis of such peaks allows determinations to be made about the makeup of the mixture which is injected into the chromatography device. Additionally, since different compounds have different retention times within the stationary phase of a chromatography device, these compounds and molecules may be separated by separate collection of the effluent during different peak elutions.

Chromatographic techniques vary by stationary phase structure, shape and orientation. Column chromatography may involve a packed column, that is, a tube packed with the stationary phase which is often a resin or bead-matrix. Alternately, column chromatography may involve an open column, that is, a tube having a stationary phase that is bonded (e.g., covalently bonded) to the inside wall of the tube and having an unobstructed opening through the length of the tube. Differences in rates of movement of components through the stationary phase are according to different retention times of the different types of components.

Planar chromatography is a separation technique in which the stationary phase is present on a plane. An analysis of the mixture is available through the observance of different rates of movement of the different components present in the mobile phase through the stationary phase of the planar chromatography device. Thin-layer and paper chromatography is widely practiced in various applications. In planar chromatography, the stationary phase may be either special chromatography paper or a thin, flat layer of an inert substrate such as silica gel, alumina, or cellulose. In paper chromatography, the sample may be applied to a polar celluloid substance. A solvent is applied to the paper. As the solvent rises through the paper, it encounters the sample mixture. The components in the sample mixture travel up the paper with the solvent, with those components that are less-polar traveling further. Different states of the mobile phases of chromatographic processes are also known with both gaseous and liquid mobile phases being used.

SUMMARY OF THE INVENTION

Principles of the invention provide, for example, semiconductor devices, chromatography devices and integrated circuits for detecting one or more molecules, and methods for forming a semiconductor device for detecting one or more molecules.

In accordance with a first aspect of the invention, a semiconductor device for detecting one or more molecules comprises a channel formed within a semiconductor structure, and at least one detector formed within the semiconductor structure. The at least one detector detects the one or more molecules in the channel. The semiconductor device may optionally comprise one or more additional channels formed within the semiconductor structure.

In accordance with a second aspect of the invention, a chromatography device for detecting one or more molecules is presented. The chromatography device comprises the above semiconductor device. The chromatography device is operative to separate at least one component from a mixture of components and/or detect at least one component in a mixture of components.

In accordance with a third aspect of the invention, an integrated circuit for detecting one or more molecules is presented. The integrated circuit comprises the above semiconductor device and a processor device coupled to the at least one detector of the semiconductor device. The at least one detector detects the one or more molecules in the channel and generates a signal responsive to the detection of the one or more molecules. The processor device is operative to generate an output based at least in part on the signal.

In accordance with a fourth aspect of the invention, a method for forming a semiconductor device for detecting one or more molecules comprises forming at least one channel within a semiconductor structure, and forming at least one detector within the semiconductor structure. The at least one detector detects the one or more molecules in the channel.

In accordance with a fifth aspect of the invention, the above semiconductor device is operative to detect, identify and/or count a single molecule as well as more than one molecule.

Advantageously, principles of the invention provide, for example, devices for detecting, quantifying and/or identifying molecules (e.g., chromatography devices) that are sensitive to small quantities of material as well as smaller molecules and components, do not require fluids at high pressure and associated pumps, and have integrated detectors thus avoiding remote detection that may reduce accuracy of measurements.

These and other features, objects and advantages of the present invention will become apparent from the following detailed description of illustrative embodiments thereof, which is to be read in connection with the accompanying drawings.

DETAILED DESCRIPTION OF THE INVENTION

Figure 1A:
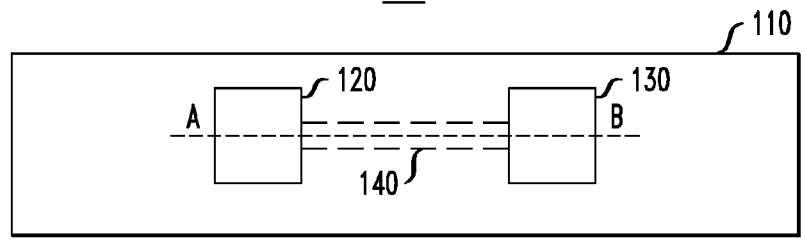
FIGS. 1a and b illustrates a nano-channel device comprising a nano-channel, a sample inlet coupled to the nano-channel and an outlet coupled to the nano-channel according to an exemplary embodiment of the invention.

Principles of the present invention will be described herein in the context of illustrative single-chip embodiments of planar nano-channels, on the scale of tens of nanometers (nm) wide, formed directly in silicon, gallium arsenide or other semiconductor, with integrated devices that allow detection of single or multiple molecules or current from single or multiple molecules. It is to be appreciated, however, that the techniques of the present invention are not limited to the specific devices and methods shown and described herein. Rather, principles of the invention are directed broadly to nano-scale devices and techniques for detecting, quantifying, identifying, and/or separating molecules and compounds (e.g., chromatography devices and techniques). For this reason, numerous modifications can be made to the embodiments shown that are within the scope of the present invention. No limitations with respect to the specific embodiments described herein are intended or should be inferred.

The term proximate or proximate to, as used herein, has meaning inclusive of, but not limited to, abutting, in contact with, and operatively in contact with. In particular and with respect to nano-channels, semiconductors and/or devices formed within semiconductors, proximate or proximate to may include, but is not limited to, being electrically coupled or coupled to. The term abut(s) or abutting, as used herein, has meaning that includes, but is not limited to, being proximate to.

The term electrode, as used herein, is an electrical conductor used to make contact with a nonmetallic part of a circuit (e.g. a semiconductor or other nonmetallic electrically conductor). The term conductor is used for conductors 420 to distinguish conductors 420 from electrodes 210; however, in the broad sense, the conductors 420 may be considered to be electrodes.

The term spectrophotometry, as used herein, is the quantifiable study of electromagnetic spectra. It may be more specific than the more-general term electromagnetic spectroscopy in that spectrophotometry deals with visible light, near-ultraviolet, and near-infrared. A spectrophotometer may be used to perform spectrophotometry. A spectrophotometer contains or has input from a photodetector or photometer (i.e., a device for measuring light intensity) and may measure light intensity as a function of the color or wavelength of the light. The spectrophotometer may contain or provide output to a light source to provide the light for detection by the photodetector. A common application of spectrophotometers is the measurement of light absorption.

There are a number of structures that lend themselves well to small scale chromatography for life sciences applications. Previous chromatography devices can often be cumbersome to use and insensitive to small quantities of materials, such as biological materials. For instance, traditional chromatography technologies can require fluids and pumps at high pressure, coupled to separate separation and detection devices that can clog and introduce variability in measurements. There is a trend to make chromatography devices smaller and more integrated, but the smallest conventional chromatographic separation devices are typically at the scale of hundreds of microns and are coupled to separate detection systems.

Embodiments of the invention may include one or more planar nano-channels, each comprising a narrow tube, for example, on the order of nanometers in diameter, lying in the plane of a substrate, such as a silicon wafer, of a device. The tube may be optionally lined with additional materials specific to the purpose of the device. The tube has an input and output opening with no additional opening along the length of the tube, except for openings specifically created for interfacing to sensors, electrodes or light sources as described herein. Having the channel in the plane of the wafer allows easy interfacing with electronic devices on or in the substrate or silicon wafer. It is understood that a nano-channel may be, for example, a planar nano-channel. Alternately, a nano-channel may not be lie in the plane of a substrate but in a plane skew to the plane of the substrate, or the nano-channel may curve or be otherwise formed so that it does not lie in a single geometric plane.

Exemplary principles of the invention are directed towards detection, quantification, identification and/or separation of molecules or types of molecules passing through one or more nano-channels. It is noted that quantification and identification of one or more molecules may include detection of the one or more molecules. That is, to count or identify the one or more molecules, the one or more molecules may need to be detected.

Several embodiments of planar nano-channels for quantification, identification, separation and/or detection of one or more molecules will be described. Exemplary embodiments of the current invention include, but are not limited to: i) nano-channels for on-chip quantification, identification, separation and/or detection of molecules; ii) planar silicon devices having direct integration of nano-channel structures with detection components; iii) nano-channels for electronic modulation of passage rate for molecular selection; and iv)

small size, enabling massively parallel operation with corresponding increases in robustness and sensitivity.

By way of non-limiting examples only, embodiments of nano-channels may identify and/or quantify components (e.g., molecules or compounds) of a mixture. One exemplary way for nano-channels to identify and quantify components uses chromatographic separation of the components for later quantification. In this case, individual molecules do not need to be counted. A current can be sensed as a mixture, or part thereof, goes through a nano-channel. The current correlates to the amount of different constituents within the mixture, or part thereof, flowing through the nano-channel. On the other hand, in a procedure that is not considered chromatographic, individual molecules may go through the nano-channel. Based on how they go through, the molecules may be counted and/or identified. This procedure does not have chromatography separation.

An exemplary feature of the invention is a nano-channel (e.g., a capillary nano-channel within a chromatography device) with a diameter small enough (e.g., less than about 100 nm) to detect single molecules or components. Another exemplary feature of the invention is a nano-channel device, according to embodiments of the invention, operative to separate at least one component from a mixture of components.

Semiconductor technologies for fabrication embodiments of the invention may be compatible with very large scale integrated (VLSI) fabrication methods used for fabricating integrated circuits, photodetectors, microelectromechanical systems (MEMS) and other semiconductor devices (e.g., transistors including field-effect transistors, capacitors, inductors, resistors and interconnects).

Using such technologies, nano-channels may be formed within a semiconductor structure. U.S. Pat. No. 7,351,648, the disclosure of which is incorporated herein by reference, describes a VLSI compatible method that can be used to form nano-channels in semiconductors.

According to principles of the present invention, various detection devices may be integrated into the semiconductor structure at least in part around or proximate to a nano-channel (e.g., a capillary chromatography nano-channel). The detection devices may include, for example, light sources, photodetectors, current measurement devices, or other sensors desired for a particular chromatography process. The integration of the detection device into the semiconductor structure comprising the nano-channel avoids problems associated with coupling of a chromatography column or channel to a separate detection device. For example, the problems associated with coupling, clogging and introducing variability into measurements can be avoided.

Nano-channels may be formed having a structure that accumulates or pools a mixture, or a portion thereof, input into the nano-channel. Optical measurements of the pooled mixture, or portion thereof, may be made. The structure that provides accumulations or pools may be, for example, a portion of a nano-channel that has a larger cross-section than another portion of the nano-channel (e.g., larger by a factor of greater than about two). For example, nano-channels may be formed having different diameters along the length of the nano-channel. The larger diameter sections of the nano-channel may accumulate or pool analyte (e.g., the analyte to be detected or measured) for better coupling to a photodetector or other detection device formed within the semiconductor proximate to the nano-channel. Alternately, nano-channels may be coupled to other structures (e.g., cavity structures) in the substrate containing pools of the mixture, or portion thereof. Optical measurements of the analyte in the pools may be made.

Certain embodiments of the invention use time of flight passage of one or more molecule through a nano-channel, or a portion of a nano-channel, in order to identify the type of molecule and/or to count the number of molecules going through the nano-channel. A detector (e.g., a photodetector and corresponding light source) may detect entrance of the one or more molecules into the nano-channel, or the portion of the nano-channel. Another detector may detect exit of the one or more molecules from the nano-channel, or the portion of the nano-channel. Transit times (i.e., times of flights) through the nano-channel, or the portion of the nano-channel, of the one or more molecules may be determined from output signals of the detectors. For example, from the output signals, how long each molecule takes to individually move through the nano-channel, or the portion of the nano-channel, may be determined. Individual detection of each molecule at the entrance and at the exit of the nano-channel, or the portion of the nano-channel, enables counting the molecules (quantification) and identifying the molecules by time of flight information. For example, a type of molecule may be identified by comparing the time of flight of that molecule with known or predetermined times of flights of various types of molecules.

Figure 2A:
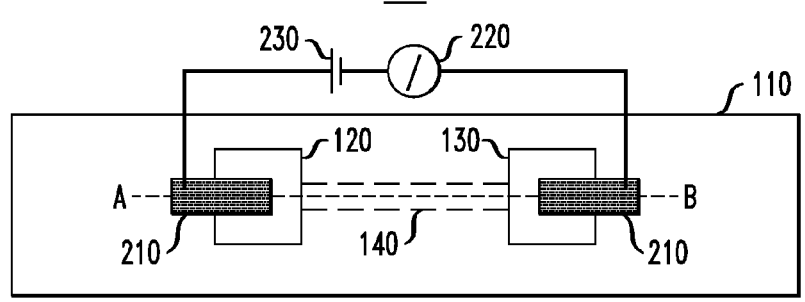
FIGS. 2a and b illustrates a nano-channel device comprising a nano-channel, a sample inlet coupled to the nano-channel, an outlet coupled to the nano-channel, and two electrodes according to an exemplary embodiment of the invention.
Figure 2B:
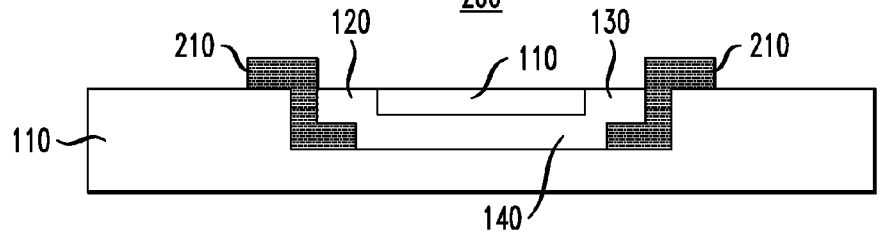
Figure 3A:
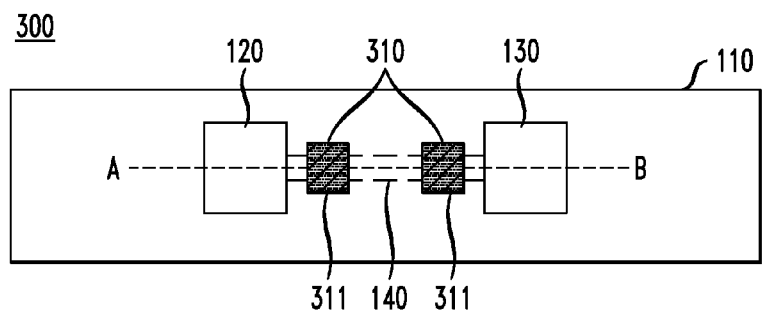
FIGS. 3a and b illustrates a nano-channel device comprising a nano-channel, a sample inlet coupled to the nano-channel, an outlet coupled to the nano-channel, and photodetectors coupled to the nano-channel according to an exemplary embodiment of the invention.
Figure 3B:
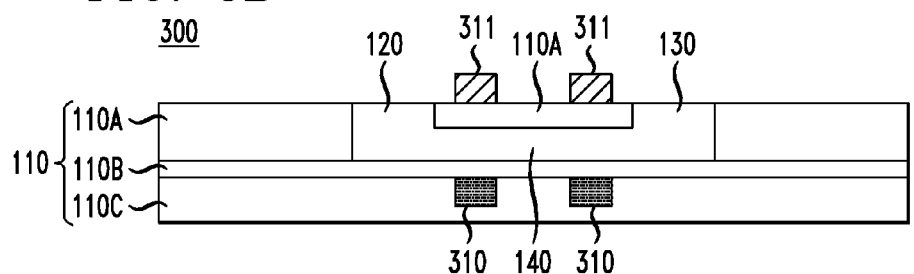

Alternately, a detector comprising a current measuring device coupled to electrodes or electrical conductors at two points in the channel (e.g., the channel inlet and the channel outlet, or two points within the channel) may provide information to determine the transit time through the nano-channel, or a portion of the nano-channel, (or the retention time within the nano-channel, or the portion of the nano-channel), therefore, determining the type of molecule. Additionally, this detector may provide information to count the number of molecules passing through the nano-channel. Nano-channel device 200 presented in FIGS. 2a and 2b, 300 presented in FIG. 3a and 3b or 400 presented in FIGS. 4a and 4b may use time of flight to identify types of molecules and quantify (e.g., quantify by type of molecule) the number of molecules passing through a nano-channel.

Devices for detection, quantification, identification and/or separation of molecules or compounds (e.g., chromatography devices), comprising many nano-channels may be formed using the above-mentioned technologies. By way of example only, an embodiment of the invention comprises a structure having hundreds or thousands of parallel nano-channels formed using fabrication technologies compatible with forming integrated circuits and/or detectors (e.g., photodetectors). Nano-channels within the semiconductor device may be formed on a single plane or on multiple planes to increase the number of integrated nano-channels. Further, distances between parallel and/or planar nano-channels may be increased to minimize cross-talk between detection devices associated with two adjacent nano-channels.

FIGS. 1-7 present illustrative examples of nano-channel devices comprising nano-channels (e.g., nano-channel 140) and formed within semiconductor structures (e.g., semiconductor structure 110) or substrates. The nano-channel devices are semiconductor devices. FIGS. 1a, 2a, 3a, 4a, and 5 are top down views of exemplary nano-channel devices. The nano-channel devices comprise nano-channels formed within the semiconductor structure 110 along an axis A-B. FIGS. 1b, 2b, 3b, 4b, and 6 are cross-sectional views of the nano-channel devices, the cross-sections including axis A-B of a nano-channel or axis A1-B1, A2-B2 and A3-B3 of three nano-channels. The semiconductor structure 110 may comprise silicon. As shown in the cross-sections of FIGS. 3b and 6, the semiconductor structure 110 may be formed having a plurality of layers (e.g., layers 110A, 110B and 110C of FIG. 3b). Alternately, the semiconductor structure 110 may comprise a single block of semiconductor wherein features are formed, for example, by etching. Processing of semiconductor structures and the forming of semiconductor structures comprising layers of semiconductors are well known in the art.

A chromatography device comprising one or more nano-channels may be operative to separate at least one component from a mixture of components and/or detect at least one component from a mixture of components. A nano-channel device according to embodiments of the present invention may, for example, be at least part of a chromatography device.

Semiconductor devices may comprise, in addition to nano-channel devices, MEMS and electronic devices which may include any of: transistors; capacitors; inductors; resistors; functional devices; processors (e.g., processor devices); and circuits and systems that may, for example, be used in conjunction with the nano-channel devices. The nano-channel devices and, optionally, the MEMS and/or the electronic devices may, for example, be formed by semiconductor processing used to form integrated circuits, sometimes known as integrated circuit or VLSI circuit processing. Such processing is well known in related art. Thus, a semiconductor structure comprising nano-channel devices as described herein and, optionally, MEMS and/or electronic devices (including detectors associated with the nano-channels) may be considered to be an integrated circuit.

Exemplary semiconductor devices comprised within the semiconductor structure 110 may comprise detectors for detecting a single molecule, more than one molecule or component of mixtures that enters a nano-channel of the nano-channel device. Exemplary detectors include photodetectors, current measuring devices and current detectors. The detectors, for example, may comprise an electronic circuit (e.g., an electronic circuit that is integrated with the nano-channel into the semiconductor device). The electronic circuit may comprise, for example, transistors, and/or a processor device. The electronic circuit may be, for example, a processing device.

In an embodiment of the invention, the nano-channel is an approximately cylindrical structure within the semiconductor structure 100. The cylindrical structure has a circular cross-section in a plane perpendicular to the axis of the cylinder. Other embodiments comprise nano-channels having channel-like or tube-like shapes other than cylindrical, for example, channels with approximately square, rectangular, oval, irregular, or other cross-sections perpendicular to the axis of the nano-channel. Further examples of nano-channel shapes are right cuboid (i.e., rectangular box), an elliptic cylinder, or a tube having an irregular shaped cross-section. A cross-section of a nano-channel, and hence the nano-channel, may be characterized by a longest dimension across the cross-section and in the plane of the cross-section, for example, the diameter of a circular cross-section or the diagonal of a rectangular cross-section. As used herein, this longest dimension across the cross-section and in the plane of the cross-section is termed a characteristic dimension of the nano-channel. For a cylindrical nano-channel, the characteristic dimension is the diameter of the cylinder, for a rectangular nano-channel, the characteristic dimension is the diagonal of the rectangular cross-section in the plane perpendicular to the longest axis of the nano-channel. The nano-channel may have, for example, an axis that is in a plane parallel to the surface of the semiconductor structure 100 or parallel to the surface of a substrate of the semiconductor structure 100.

In one embodiment, the characteristic dimension of the nano-channel may be relatively small, for example, less than about 100 nm. Certain embodiments may comprise one or more nano-channels having a characteristic dimension less than about 10 nm, or even less than about 1 nm. However, embodiments of the invention are not restricted to such small dimensions but may comprise nano-channels having a characteristic dimension greater than about 100 nm.

Certain embodiments of the invention comprise a selective coating on all or a portion of the interior wall of the nano-channel. The coating may: provide, enhance or assist in discriminating or differentiating different molecules; provide a better gradient (e.g., concentration gradient of at least one of different types of molecules) in a chromatographic device; provide greater separation of components (e.g., different types of molecules of a mixture) of a mixture of molecules; and/or improve the discriminatory power of transit time through at least a portion of the nano-channel in identifying molecules. For example, nano-channels of nano-channel devices shown in FIGS. 1a, 1b, 2a, 2b, 2a, 3b, 4a, 4b, 5, 6, 8 and 9 may have the coating. The coating may comprise, for example, an immiscible liquid coating at least a portion of the interior wall of the nano-channel, a thin film of liquid bonded to at least a portion of the surface of the interior wall of the nano-channel or a solid film coating at least a portion of the interior wall of the nano-channel.

FIGS. 1a and b depict a nano-channel device 100 comprising a nano-channel 140, a sample inlet 120 coupled to the nano-channel 140 and an outlet 130 coupled to the nano-channel 140, according to an exemplary embodiment of the invention. Nano-channel device 100 may be, for example, a device for the detection, quantification, identification and/or separation of molecules or compounds (e.g., a chromatography device). The sample inlet 120 provides a sample to the nano-channel 140. The outlet 130 is for at least a portion of the sample (effluent) to leave the channel after the effluent has passed through the nano-channel 140.

Figure 1B:
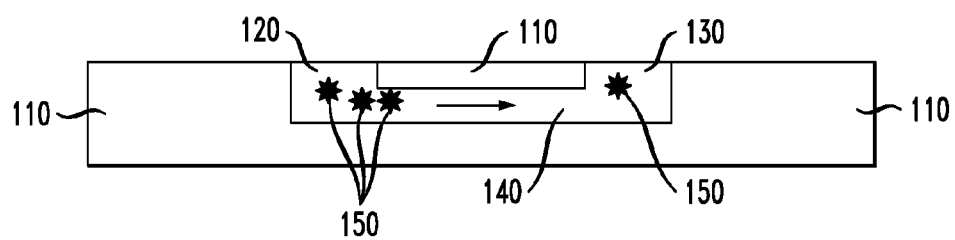

In FIG. 1b identification, quantification and/or identification of molecules or chromatography is shown occurring within the nano-channel 140. Analyte molecules 150 of a sample are entered into the sample inlet 120. At least analyte molecules 150 (e.g., analyte molecules to be detected, separated or measured) flow through the nano-channel 140 and are eluted through the outlet 130 as effluent. In one illustrative embodiment, the analyte molecules 150, or at least a portion of thereof (e.g., the analyte to be detected, separated or measured), are moved through the nano-channel 140 by an electric gradient. The electric gradient may be used to modulate a molecule passage rate for molecular selection. In another illustrative embodiment, the analyte molecules 150, or at least a portion of thereof (e.g., the analyte to be detected, separated or measured), are moved through the nano-channel 140 by a pressure gradient. This gradient is established from the sample inlet 120 to the outlet 130 by pressurization of the input sample (e.g., liquid or gas input sample). The gradient sets up a corresponding gradient of molecular species based on intrinsic properties such as size or hydrophobicity.

FIGS. 2a and b depict a nano-channel device 200 comprising a nano-channel 140, a sample inlet 120, an outlet 130, and two electrodes 210, according to an exemplary embodiment of the invention. Nano-channel device 200 may be, for example, a device for the detection, quantification, identification and/or separation of molecules or compounds (e.g., a chromatography device). The two electrodes 210 are coupled to the ends of nano-channel 140 and formed in the sample inlet 120 and outlet 130. In an illustrative embodiment, electrodes 210 may be used to apply an electric potential or an electric gradient to or across the nano-channel 140. The electric potential or gradient may be used to control the flow of a charged mixture through the nano-channel 140. The electric gradient is established by an electric field along the length of the nano-channel.

The electrodes 210 may also be electrically coupled to a current-measuring device (detector) 220 operative to monitor or determine the retention time of one or more molecules inside the nano-channel 140 by monitoring or determining ionic current through the nano-channel 140. The current-measuring device 220 is electrically coupled to one of the electrodes 210 (e.g., the electrode 210 at the outlet 130) and to a voltage source 230. The voltage source 230 is electrically coupled to the other electrode 210 (e.g., the electrode 210 at the sample inlet 120). The voltage source 230 may supply voltage to form the electric gradient. The voltage source 230 may be considered an electrical current source to provide current to form the electric gradient.

Note that current measuring device 220 coupled to the electrodes 210 may function to count either or both individual molecules as discrete events exhibited by transient currents (e.g., current spikes), or bulk flow of molecules (e.g., multiple molecules) exhibited as a more continuous current flow.

The current measurement device 220 may be integrated within the semiconductor structure 110 along with the nano-channel device 200, coupled to the nano-channel 140, and operative to measure electrical current through the nano-channel 140. The voltage source may, but is not necessarily, integrated into the semiconductor structure 110. Examples of integrated voltage sources include solar cells and electromagnetic or radio frequency (RF) induction voltage sources.

FIGS. 3a and b depict a nano-channel device 300 comprising a nano-channel 140, a sample inlet 120, an outlet 130, and one or more photodetectors 310 coupled to the nano-channel according to an exemplary embodiment of the invention. In FIGS. 3a and 3b, two photodetectors 310 are shown coupled to the nano-channel below the nano-channel. Nano-channel device 300 may be, for example, a device for the detection, quantification, identification and/or separation of molecules or compounds (e.g., a chromatography device). Photodetectors 310 are integrated with the nano-channel device, optically coupled to the nano-channel 140, and are operative to perform optical measurements (e.g., optical lens-free measurements) of analyte molecules (e.g., the analyte to be detected, separated or measured), from a sample entered into the inlet 120. Photodetectors 310 may be positioned or integrated either above or below the nano-channel 140. In an illustrative embodiment, the photodetectors 310 may comprise Single-Photon Avalanche Diodes (SPADs) capable of detecting low-intensity signals. The photodetectors 210 may sense light and/or changes in illumination of light within the nano-channel 140. The photodetectors 210 may not necessarily include focusing optics.

Although the nano-channel device 300 is illustrated in FIGS. 3a and 3b with two photodetectors 310, embodiments of the invention are not so limited. Embodiments are contemplated having only one photodetector 310 and having three or more photodetectors 310.

Photodetectors 310 may be formed below the nano-channel as shown, for example, during early stages of semiconductor processing commonly known as front-end-of-the-line (FEOL) portion of the semiconductor process. Photodetectors 310 may be formed above the nano-channel (photodetectors 310 are not shown above the nano-channel), for example, using a wafer-bonding process. Photodetectors 310 may have semiconductor material between the photodetectors 310 and the nano-channel 140 as shown in FIG. 3b, or may form part of the walls of the nano-channel 140. The semiconductor material between photodetectors 310 and the nano-channel 140 allows passage of light between the nano-channel 140 and the photodetectors 310.

By way of a non-limiting example only, light may be introduced into the nano-channel by one, two or more light sources 311. As shown in FIGS. 3a and 3b, the light source 311 may be coupled to the top of the nano-channel 140 and positioned approximately directly across the nano-channel 140 from the photodetectors 310. The light sources 311 may provide light for detection by photodetectors 310. The light may pass through analyte within the nano-channel 140. As shown in FIGS. 3a and 3b, with two photodetectors 310 coupled to the bottom of the nano-channel 140 and two light sources 311 coupled to the top of the nano-channel 140 and with each light source 311 about directly across the nano-channel 140 from a photodetector 310, two portions of the nano-channel 140 are illuminated by the light sources 311. The light, after passing through analyte within the nano-channel 140, is detected by the corresponding photodetector 310. A photodetector 310 and a corresponding light source 311 for providing illumination for detection by the photodetector 310 may be considered a detector unit an optical detector unit or simply an optical detector or detector.

For one example, one or both light sources 311 may provide light from, or in conjunction with, a spectrophotometer. The light sources 311 may be coupled to and/or considered part of the spectrophotometer. The photodetectors 310 may be coupled to the spectrophotometer, may provide input to at least part of the spectrophotometer and/or may be considered the light sensing part (i.e., photodetector) of the spectrophotometer.

For another example, each light source may be a laser. The nano-channel device may further comprise the light sources 310 (e.g., lasers or light sources providing light form or in conjunction with a spectrophotometer).

As described above, the nano-channel device 300 may use time of flight to identify types of molecules and quantify (e.g., quantify by type of molecule) the number of molecules passing through the nano-channel 140.

Figure 4A:
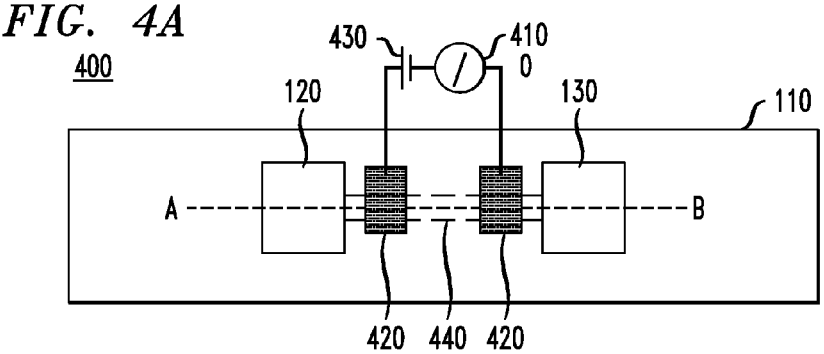
FIGS. 4a and b illustrates a nano-channel device comprising a nano-channel, a sample inlet coupled to the nano-channel, an outlet coupled to the nano-channel, and conductors coupled to the nano-channel according to an exemplary embodiment of the invention.

FIGS. 4a and b show a nano-channel device 400 comprising a nano-channel 440, a sample inlet 120, an outlet 130, and electrical conductors 420 coupled to the nano-channel 440 according to an exemplary embodiment of the invention. The nano-channel device 400 is coupled to a current measuring device 410 and a voltage source 430. Nano-channel device 400 may be, for example, a device for the detection, quantification, identification and/or separation of molecules or compounds (e.g., a chromatographic device). The current-measuring device 410 is electrically coupled to one of the conductor 420 (e.g., the conductor 420 towards the outlet 130) and to the voltage source 430. The voltage source 430 is electrically coupled to the other conductor 420 (e.g., the conductor 420 towards the sample inlet 120). The voltage source 430 may supply voltage to form the electric gradient. The voltage source 430 may be considered an electrical current source to provide current to form the electric gradient.

The nano-channels 440 are similar to the nano-channels 140 except the conductors 420 may form a portion of the wall of nano-channel 440. The conductors 420 may comprise, for example, metal and/or semiconductor material.

The nano-channel device 400 is similar to nano-channel device 200 in that the conductors 420 are similar to the electrodes 210 as the conductors 420 may be used for establishing an electric gradient in the nano-channel 440 by an electric field along the length of the nano-channel. The electric gradient may be used to control the flow of a charged mixture through the nano-channel 440. However, the nano-channel device 400 differs from the nano-channel device 200 in that the conductors 420 may be positioned at the ends of or further within the length of the nano-channel 440, wherein the electrodes 210 are positioned at or near the ends of the nano-channel 440 within the sample inlet 120 and outlet 130. Consequently, for nano-channel device 400 the electric gradient and the electric field are within that portion of the nano-channel 440 that is between the conductors 420, whereas for nano-channel device 200 the electric gradient and the electric field may extend the entire length of the nano-channel.

Figure 4B:
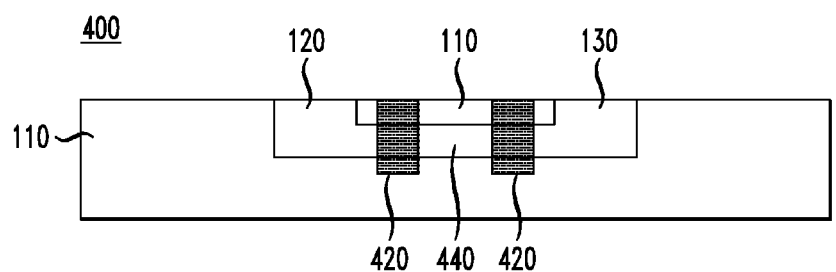

As shown in FIGS. 4a and b, the conductors 420 may be coupled to the nano-channel 440, at, proximate to, or towards the ends of nano-channel 440. By way of example only, a conductor 440 may form a continuous ring around and the nano-channel 440, form a single point contact to nano-channel 440, or form multiple (e.g., two) point contacts with nano-channel 440. Conductor 420 may form a portion of the wall of nano-channel 440 and may be in physical, as well as electrical, contact with a sample, or components flowing through nano-channel 440. As shown in FIGS. 4a and 4b, the conductors 420 are continuous around nano-channel 440. Alternately, the conductors 420 could contact the nano-channel only at a portion of the circumference around the nano-channel 440 (e.g., at the top of the nano-channel 440). Note that current measuring device 410 coupled to conductors 420 may function to count either or both individual molecules as discrete events exhibited by transient currents (e.g., current spikes), or bulk flow of molecules (e.g., multiple molecules) exhibited as a more continuous current flow.

The current measurement device 410 may be integrated within the semiconductor 110 along with the nano-channel device, coupled to the nano-channel 140, and operative to measure electrical current through the nano-channel 140. In an illustrative embodiment, conductors 420 may be formed within the nano-channel through an atomic layer deposition (ALD) process. The voltage source may, but is not necessarily, integrated into the semiconductor structure 110.

Figure 5:
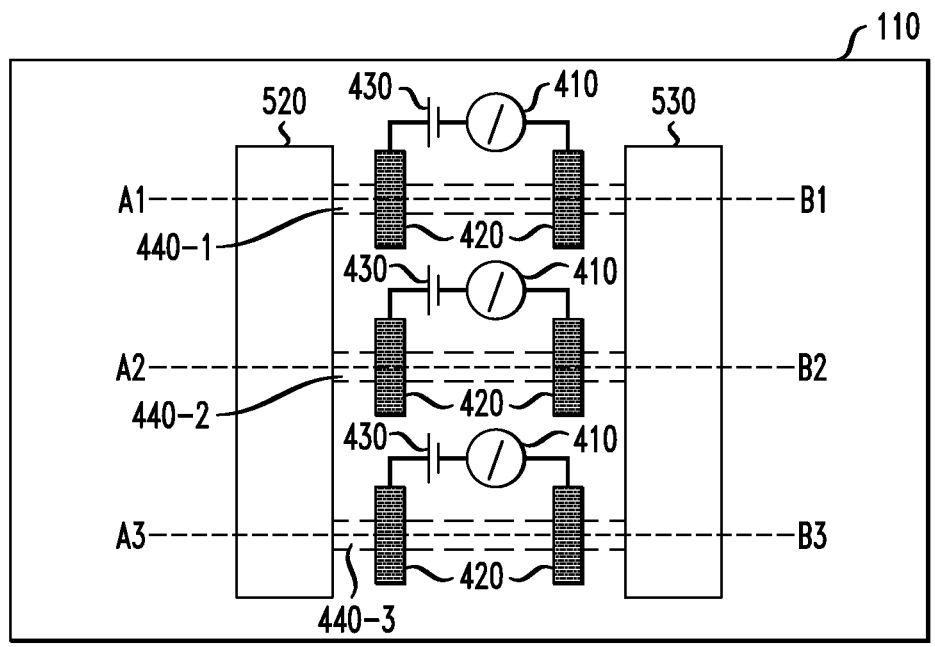
FIG. 5 shows a top view of an exemplary, multi-channel nano-channel device comprising multiple, approximately parallel nano-channels, conductors, a common sample inlet and a common outlet, according to an embodiment of the invention.

FIG. 5 shows a top view of a nano-channel device 500 comprising three approximately parallel nano-channels 440-1, 440-2 and 440-3, conductors 420, a common sample inlet 520 and a common outlet 530 according to an embodiment of the invention. Each of the nano-channels 440-1, 440-2 and 440-3 may be coupled to a detector, for example, a photodetector (not shown) or a current measuring device 410. Each nano-channel 440-1, 440-2 and 440-3 coupled to a current measuring device 410 may also be coupled to a voltage source 430 as was described with reference to FIG. 4a and b, and as shown in FIG. 5. In a particular embodiment, some of the nano-channels are coupled to a first type of detector, for example, a photodetector, and some of the nano-channels are coupled to a second type of detector, for example, a current measuring device with or without a coupled voltage source. Nano-channel device 500 may be, for example, a device for the detection, quantification, identification and/or separation of molecules or compounds (e.g., a chromatography device). Each of the three current measuring devices 410 and the voltage sources 430, along with associated conductors 420, is similar to (e.g., similar to regarding integration, placement, coupling and function) the current measuring device 410 and the voltage source 430, along with associated conductors 420, of the nano-channel device 400. The common sample inlet 520 is coupled to, and provides the sample to, all three nano-channels 440. The common outlet 530 is coupled to, and allows for egress of the effluent from, all three nano-channels 440. Advantageously, the distance between the nano-channels may be increased to reduce channel cross-talk between the channels. In an additional aspect of the invention, the three nano-channels 440-1, 440-2 and 440-3 may be formed having axis (A1-B1, A2-B2 and A3-B3) substantially within a common plane, for example, a common plane substantially parallel to an upper surface of the semiconductor structure 110.

Although the illustrative embodiment of nano-channel device 500 comprises three nano-channels 440-1, 440-2 and 440-3, other embodiments of the invention are not so limited. Other embodiments are contemplated that comprise more than three nano-channels 440 or comprise just two nano-channels 440. A large number of nano-channels 440 (e.g., up to thousands) is advantageous to improve the accuracy, robustness and/or sensitivity. Although the illustrative embodiment of nano-channel device 500 comprises three substantially parallel nano-channels 440-1, 440-2 and 440-3, other embodiments of the invention are not so limited and may comprise nano-channels 440 that are not parallel.

Figure 6:
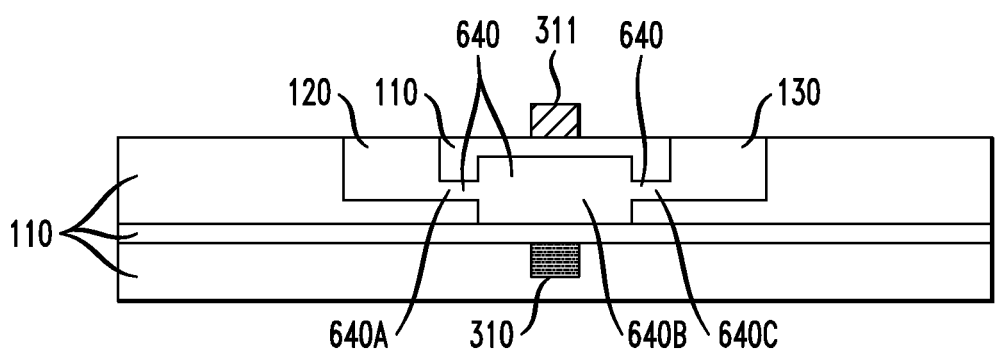
FIG. 6 shows a cross-sectional view of a nano-channel device comprising a nano-channel having at least two cross-sectional areas, a sample inlet, and outlet, according to an embodiment of the invention.

FIG. 6 shows a cross-sectional view of a nano-channel device 600 comprising a nano-channel 640, a sample inlet 120, and an outlet 130, according to an embodiment of the invention. The exemplary nano-channel device 600 is coupled to photodetector 310. The nano-channel device 600 may be, for example, a device for the detection, quantification, identification and/or separation of molecules or compounds (e.g., a chromatography device). The nano-channel device 600 is similar to nano-channel device 100 except for the shape of the nano-channel 640. The nano-channel 640 comprises a first portion 640A, a second portion 640B and a third portion 640C. The first portion 640A is coupled to, and receives a sample from, the sample inlet 120. The second portion 640B is coupled to, and receives at least part of the sample from, the first portion 640A. The third portion 640C is coupled to, and receives at least a portion of the sample from, the second portion 640B. The outlet 130 is coupled to, and receives at least a portion of the sample (effluent) from the third portion 640C. The second portion 640B has a diameter, critical dimension or cross-sectional area larger than the diameter, critical dimension or cross-sectional area of the third portion 640C, and, optionally, larger than the diameter or cross-sectional area of the first portion 640A. In this way, the nano-channel device 600 has a modulated diameter, critical dimension or cross-sectional area of the nano-channel 640. Different nano-channel diameters, critical dimension or cross-sectional areas may be formed by semiconductor processing known in the art. The wider second portion 640B accumulates analyte for better detection by the photodetectors 310.

The nano-channel device 600 is similar to nano-channel device 300 in that it comprises at least one photodetector 310 and may receive light from light source 311. In the nano-channel device 600, the placement, operation and number of photodetectors 310 and light sources 311 are similar to the placement, operation and number of photodetectors 310 and light sources 311 in nano-channel device 300, except that in nano-channel device 600, the photodetectors 310 and light sources 311 may be positioned on the wider portion (e.g., the second portion 640B) or the pooling portion of the nano-channel 640.

Nano-channel device 600 may be considered as an example of a nano-channel device that provides pooling (e.g., accumulating of analyte) and optical measurement of an analyte in a portion of the pooling portion of the nano-channel. Another embodiment of a nano-channel device that provides pooling (e.g., accumulating of analyte) is a device that has a separate pooling structure in the semiconductor structure 100. The separate pooling structure is in place of, or in addition to, the portion of a nano-channel having a larger cross-sectional area. The pooling structure may be, for example, one or more cavities in the semiconductor structure 100, the one or more cavities coupled to the nano-channel and configured to at least partially fill with at least a portion of the analyte (i.e., sample). The pooling structure is coupled to the nano-channel which provides the analyte to the pooling structure and may provide for egress of the analyte from the pooling structure. In this embodiment, one or more photodetectors and light sources may be positioned proximate to or coupled to the pooling structure for optical measurement or analysis of the analyte. Pooling of analyte provides a greater quantity of analyte for optical measurement.

Although the nano-channel device 600 is illustrated in FIG. 6 coupled to one photodetectors 310 and one light source 311, embodiments of the invention are not so limited. Embodiments are contemplated having only more than one photodetector 310 and light source 311.

Figure 7:
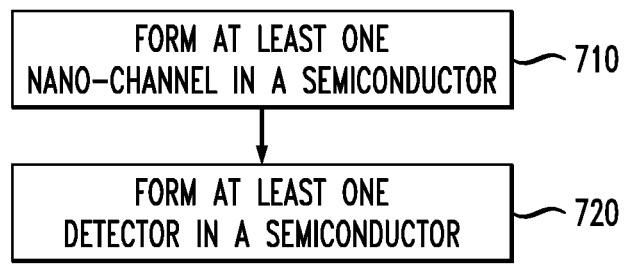
FIG. 7 depicts a flow diagram illustrating a method for forming a semiconductor device for detecting one or more molecules according to an embodiment of the invention.

FIG. 7 depicts a flow diagram illustrating a method for forming a semiconductor device for detecting one or more molecules according to an embodiment of the invention. At step 710, at least one nano-channel is formed within a semiconductor structure. In step 720 at least one detector is formed within the semiconductor structure. The at least one detector detects the one or more molecules of a sample entering the at least one nano-channel.

Figure 8:
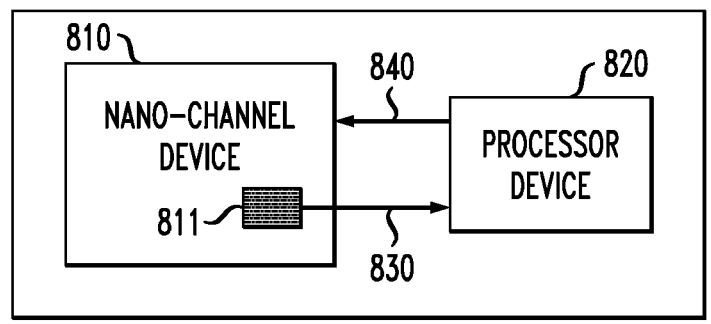
FIG. 8 shows a semiconductor device, such as an integrated circuit, comprising a nano-channel device and a processor device according to an embodiment of the invention.

FIG. 8 shows a semiconductor device 800, such as an integrated circuit, comprising a nano-channel device 810 (e.g., nano-channel device 200, 300, 400, 500 or 600) and a processor device 820 according to an embodiment of the invention. The semiconductor device or integrated circuit is operative to detect one or more molecules of a sample entering one or more channels of the nano-channel device 810. The nano-channel device 810 comprises at least one detector 811 to detect the one or more molecules and to provide an electrical signal 830 output from the nano-channel device. The output of the nano-channel device 820 is coupled to the processor device 820 at an input to the processor device 820. The signal 830 is responsive to detection of the one or more molecules. The processor device 820 is configured to generate an output based at least in part on the signal 830. In some embodiments, the processor device 820 may provide automated or semi-automated control of the nano-channel device 810 via an electrical control signal 840 further coupling the processor device 820 to the nano-channel device 810. The control signal 840 may, for example, control the voltage source 230 (FIG. 2a) or voltage source 430 (FIG. 4a or 5).

It is to be appreciated that because dies are diced from wafers, dies comprising one or more nano-channel devices according to embodiments of the present invention are considered part of the present invention.

At least a portion of the techniques or structures of the present invention, for example, the techniques or structures illustrated in FIGS. 1-8, may be implemented in one or more integrated circuits. In forming integrated circuits, die are typically fabricated in a repeated pattern on a surface of a semiconductor wafer. Individual die are cut or diced from the wafer, then packaged as integrated circuits. One skilled in the art would know how to dice wafers and package die to produce integrated circuits. Integrated circuits so manufactured are considered part of this invention.

Figure 9:
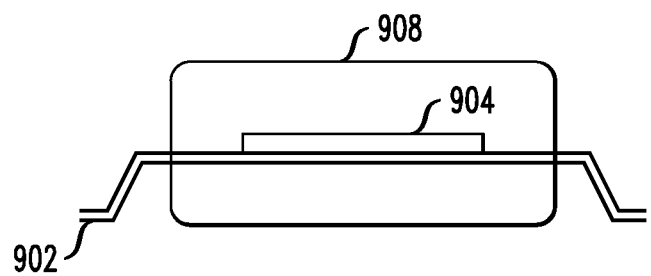
FIG. 9 is a cross-sectional view depicting an exemplary packaged integrated circuit according to an embodiment of the present invention.

FIG. 9 is a cross-sectional view depicting an exemplary packaged integrated circuit 900 according to an embodiment of the present invention. The packaged integrated circuit 900 comprises a leadframe 902, a die 904 attached to the leadframe, and a plastic encapsulation mold 908. Although FIG. 9 shows only one type of integrated circuit package, the invention is not so limited; the invention may comprise an integrated circuit die enclosed in any package type.

The die 904 includes a device described herein, and may include other structures or circuits. For example, the die 904 includes at least one via according to embodiments of the invention.

An integrated circuit in accordance with the present invention can be employed in applications, hardware and/or electronic systems. Suitable hardware and systems for implementing the invention may include, but are not limited to, personal computers, communication networks, electronic commerce systems, portable communications devices (e.g., cell phones), solid-state media storage devices, functional circuitry, etc. Systems and hardware incorporating such integrated circuits are considered part of this invention. Given the teachings of the invention provided herein, one of ordinary skill in the art will be able to contemplate other implementations and applications of the techniques of the invention.

It will be appreciated and should be understood that the exemplary embodiments of the invention described above can be implemented in a number of different fashions. Given the teachings of the invention provided herein, one of ordinary skill in the related art will be able to contemplate other implementations of the invention. Indeed, although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A semiconductor device for detecting one or more molecules, the semiconductor device comprising:
 a channel formed within a semiconductor structure; and
 at least one detector formed within the semiconductor structure;
 wherein the at least one detector is configured to detect the one or more molecules in the channel;
 wherein the channel comprises:
 a first end coupled to a sample inlet;
 a second end coupled to a sample outlet;
 a first section having a first diameter, the first section extending from the sample inlet to a first point in the channel;
 a second section having a second diameter, the second diameter being greater than the first diameter, the second section extending from the first point to a second point in the channel; and
 a third section having a third diameter, the third diameter being smaller than the second diameter, the third section extending from the second point to the sample outlet;
 wherein the sample inlet is configured to provide a sample comprising the one or more molecules to the channel, the sample inlet coupled to one end of the channel and the sample outlet is configured for at least a portion of the sample to leave the channel; and
 wherein the semiconductor device further comprises one or more additional channels formed within the semiconductor structure, wherein one end of each of the one or more additional channels is coupled to the sample inlet and another end of the each of the one or more additional channels is coupled to the sample outlet, and wherein the one or more additional channels is coupled to one or more associated additional detectors.

2. The semiconductor device of claim 1 further comprising:
 a first electrode proximate to the sample inlet; and
 a second electrode proximate to the outlet.

3. The semiconductor device of claim 2, wherein the first electrode and the second electrode are used for at least one of: (i) applying an electric potential to the channel; and (ii) measuring an electric current through the channel.

4. The semiconductor device of claim 1 further comprising at least two conductors coupled to the channel.

5. The semiconductor device of claim 4, wherein the at least two conductors are used for at least one of: (i) applying an electric potential to at least a portion of the channel; and (ii) measuring an electric current through the at least a portion of the channel.

6. The semiconductor device of claim 4, wherein the at least two conductors form a portion of a wall of the channel.

7. The semiconductor device of claim 1, wherein the semiconductor device is operative to detect a single molecule.

8. The semiconductor device of claim 1, wherein the channel is one of: a cylinder, an elliptic cylinder, a right cuboid, and a tube with an irregular shaped cross-section, and wherein a characteristic dimension is the longest dimension across a cross-section of the channel, the cross-section being approximately at right angles to axis of the channel, the characteristic dimension less than at least one of: about 100 nanometers, about 10 nanometers, about 1 nanometer.

9. The semiconductor device of claim 1 wherein the channel and of the one or more additional channels are about parallel and have axis substantially residing within a common plane.

10. The semiconductor device of claim 1, wherein at least one of the first section, the second section and the third section has a respective diameter which varies along its length.

11. The semiconductor device of claim 1, wherein at least a portion of the sample is moved through the channel by an electric gradient established by an electric field along the length of the channel.

12. The semiconductor device of claim 1, wherein at least a portion of the sample is moved through the channel by a pressure gradient.

13. The semiconductor device of claim 1, wherein the semiconductor structure comprises silicon.

14. The semiconductor device of claim 1 operative to at least one of: (i) separate at least one component from a mixture of components; (ii) identify the one or more molecules; and (iii) count a number of the one or more molecules.

15. The semiconductor device of claim 1 further comprising a cavity within the semiconductor structure, the cavity coupled to the channel and configured to at least partially fill with at least a portion of the sample.

16. A semiconductor device for detecting one or more molecules, the semiconductor device comprising:
a channel formed within a semiconductor structure; and
at least one detector formed within the semiconductor structure;
wherein the at least one detector is configured to detect the one or more molecules in the channel;
wherein the channel comprises:
a first end coupled to a sample inlet;
a second end coupled to a sample outlet;
a first section having a first diameter, the first section extending from the sample inlet to a first point in the channel;
a second section having a second diameter, the second diameter being greater than the first diameter, the second section extending from the first point to a second point in the channel; and
a third section having a third diameter, the third diameter being smaller than the second diameter, the third section extending from the second point to the sample outlet; and
wherein the at least one detector comprises a current-measuring device operative to determine a retention time of the one or more molecules inside the channel by determining ionic current through the channel.

17. A semiconductor device for detecting one or more molecules, the semiconductor device comprising:
a channel formed within a semiconductor structure; and
at least one detector formed within the semiconductor structure;
wherein the at least one detector is configured to detect the one or more molecules in the channel;
wherein the channel comprises:
a first end coupled to a sample inlet;
a second end coupled to a sample outlet;
a first section having a first diameter, the first section extending from the sample inlet to a first point in the channel;
a second section having a second diameter, the second diameter being greater than the first diameter, the second section extending from the first point to a second point in the channel; and
a third section having a third diameter, the third diameter being smaller than the second diameter, the third section extending from the second point to the sample outlet; and
wherein the at least one detector comprises at least one of: (i) at least one photodetector operative to sense light within the channel; and (ii) at least one light source operative to supply the light into the channel.

18. A semiconductor device for detecting one or more molecules, the semiconductor device comprising:
a channel formed within a semiconductor structure; and
at least one detector formed within the semiconductor structure;
wherein the at least one detector is configured to detect the one or more molecules in the channel;
wherein the channel comprises:
a first end coupled to a sample inlet;
a second end coupled to a sample outlet;
a first section having a first diameter, the first section extending from the sample inlet to a first point in the channel;
a second section having a second diameter, the second diameter being greater than the first diameter, the second section extending from the first point to a second point in the channel; and
a third section having a third diameter, the third diameter being smaller than the second diameter, the third section extending from the second point to the sample outlet;
wherein at least one of the first section, the second section and the third section has a respective diameter which varies along its length; and
wherein at least one of: (i) a photodetector is coupled to the first section of the channel; and (ii) a light source is coupled to the first section of the channel.

19. A semiconductor device for detecting one or more molecules, the semiconductor device comprising:
a channel formed within a semiconductor structure; and
at least one detector formed within the semiconductor structure;
wherein the at least one detector is configured to detect the one or more molecules in the channel;
wherein the channel comprises:

a first end coupled to a sample inlet;
a second end coupled to a sample outlet;
a first section having a first diameter, the first section extending from the sample inlet to a first point in the channel;
a second section having a second diameter, the second diameter being greater than the first diameter, the second section extending from the first point to a second point in the channel; and
a third section having a third diameter, the third diameter being smaller than the second diameter, the third section extending from the second point to the sample outlet; and
wherein the semiconductor device further comprises a coating on an interior wall of at least a portion of the channel, the coating assisting in at least one of: (i) discrimination between the one or more molecules; (ii) a concentration gradient of the one or more molecules in a chromatographic device; and (iii) separation of components of a mixture, the mixture comprising the one or more molecules.

20. A semiconductor device for detecting one or more molecules, the semiconductor device comprising:
a channel formed within a semiconductor structure; and
at least one detector formed within the semiconductor structure;
wherein the at least one detector is configured to detect the one or more molecules in the channel;
wherein the channel comprises:
a first end coupled to a sample inlet;
a second end coupled to a sample outlet;
a first section having a first diameter, the first section extending from the sample inlet to a first point in the channel;
a second section having a second diameter, the second diameter being greater than the first diameter, the second section extending from the first point to a second point in the channel; and
a third section having a third diameter, the third diameter being smaller than the second diameter, the third section extending from the second point to the sample outlet; and
wherein the detector comprises a first electrode and a second electrode placed at respective first and second positions in the channel, the detector being configured to determine a time taken by one or more molecules to pass through at least a portion of the channel and
wherein said time taken is used to at least one of: (i) identify the one or more molecules; and (ii) count a number of the one or more molecules going through the channel.

21. A chromatography device for detecting one or more molecules, the chromatography device comprising:
a channel formed within a semiconductor structure; and
at least one detector formed within the semiconductor structure;
wherein the at least one detector is configured to detect the one or more molecules in the channel; and
wherein the chromatography device is operative to at least one of: (i) separate at least one component from a mixture of components; and (ii) detect at least one component in a mixture of components; and
wherein the channel comprises:
a first end coupled to a sample inlet;
a second end coupled to a sample outlet;
a first section having a first diameter, the first section extending from the sample inlet to a first point in the channel;
a second section having a second diameter, the second diameter being greater than the first diameter, the second section extending from the first point to a second point in the channel; and
a third section having a third diameter, the third diameter being smaller than the second diameter, the third section extending from the second point to the sample outlet.

22. An integrated circuit operative to detect one or more molecules, the integrated circuit comprising:
at least one channel formed within a semiconductor structure;
at least one detector formed within the semiconductor structure, wherein the at least one detector is configured to detects the one or more molecules in the channel and generates a signal responsive to the detection of the one or more molecules; and
a processor device coupled to the at least one detector and operative to generate an output based at least in part on the signal; and
wherein the channel comprises:
a first end coupled to a sample inlet;
a second end coupled to a sample outlet;
a first section having a first diameter, the first section extending from the sample inlet to a first point in the channel;
a second section having a second diameter, the second diameter being greater than the first diameter, the second section extending from the first point to a second point in the channel; and
a third section having a third diameter, the third diameter being smaller than the second diameter, the third section extending from the second point to the sample outlet;
wherein the sample inlet is configured to provide a sample comprising the one or more molecules to the channel, the sample inlet coupled to one end of the channel and the sample outlet is configured for at least a portion of the sample to leave the channel; and
wherein the integrated circuit further comprises one or more additional channels formed within the semiconductor structure, wherein one end of each of the one or more additional channels is coupled to the sample inlet and another end of the each of the one or more additional channels is coupled to the outlet, and wherein the one or more additional channels is coupled to one or more associated additional detectors.

23. A method for forming a semiconductor device for detecting one or more molecules, the method comprising:
forming at least one channel within a semiconductor structure; and
forming at least one detector within the semiconductor structure;
wherein the at least one detector is configured to detect the one or more molecules in the channel;
wherein the channel comprises:
a first end coupled to a sample inlet;
a second end coupled to a sample outlet;
a first section having a first diameter, the first section extending from the sample inlet to a first point in the channel;
a second section having a second diameter, the second diameter being greater than the first diameter, the second section extending from the first point to a second point in the channel; and a third section having a third diameter, the third diameter being smaller than the second diameter, the third section extending from the second point to the sample outlet;

wherein the sample inlet is configured to provide a sample comprising the one or more molecules to the channel and the sample outlet is configured for at least a portion of the sample to leave the channel; and wherein the method further comprises forming one or more additional channels formed within the semiconductor structure, wherein one end of each of the one or more additional channels is coupled to the sample inlet and another end of the each of the one or more additional channels is coupled to the outlet, and wherein the one or more additional channels is coupled to one or more associated additional detectors.

* * * * *